US 9,028,398 B2

(12) United States Patent
Kumar et al.

(10) Patent No.: US 9,028,398 B2
(45) Date of Patent: *May 12, 2015

(54) SYSTEM FOR EVACUATING DETACHED TISSUE IN CONTINUOUS FLOW IRRIGATION ENDOSCOPIC PROCEDURES

(76) Inventors: Alka Kumar, Jaipur (IN); Atul Kumar, Jaipur (IN)

( * ) Notice: Subject to any disclaimer, the term of this patent is extended or adjusted under 35 U.S.C. 154(b) by 2027 days.

This patent is subject to a terminal disclaimer.

(21) Appl. No.: 11/870,267

(22) Filed: Oct. 10, 2007

(65) Prior Publication Data

US 2008/0091071 A1    Apr. 17, 2008

(30) Foreign Application Priority Data

Oct. 11, 2006   (IN) .......................... 2237/DEL/2006

(51) Int. Cl.
| | |
|---|---|
| A61B 1/12 | (2006.01) |
| A61B 1/00 | (2006.01) |
| A61B 1/04 | (2006.01) |
| A61B 1/015 | (2006.01) |
| A61M 1/00 | (2006.01) |
| A61M 3/02 | (2006.01) |
| F04B 43/12 | (2006.01) |

(52) U.S. Cl.
CPC .............. *A61B 1/015* (2013.01); *A61B 1/00068* (2013.01); *A61B 1/00071* (2013.01); *A61B 1/00094* (2013.01); *A61M 1/0031* (2013.01); *A61M 1/0058* (2013.01); *A61M 3/0258* (2013.01); *A61M 2205/3337* (2013.01); *F04B 43/1253* (2013.01)

(58) Field of Classification Search
CPC ........... A61B 1/00094; A61B 1/00119; A61B 1/012; A61B 1/015; A61B 1/018; A61B 1/12; A61B 1/128; A61B 1/303; A61B 1/307; A61B 17/32; A61B 17/32002; A61B 17/320016
USPC ................. 600/105, 155–159, 121–125, 153; 604/19, 30–35, 65–67; 606/170, 171, 606/180
See application file for complete search history.

(56) References Cited

U.S. PATENT DOCUMENTS

| | | |
|---|---|---|
| 3,835,842 A | 9/1974 | Iglesias |
| 5,052,900 A | 10/1991 | Austin |
| 5,320,091 A | 6/1994 | Grossi et al. |

(Continued)

FOREIGN PATENT DOCUMENTS

| | | |
|---|---|---|
| WO | WO 99/11184 | 3/1999 |
| WO | WO 2006/021872 A2 | 3/2006 |

*Primary Examiner* — Ryan Henderson
(74) *Attorney, Agent, or Firm* — Dickstein Shapiro LLP

(57) ABSTRACT

A continuous flow irrigation endoscope and a continuous flow irrigation fluid management system, both designed to be compatible to each other and to function as a single system. The endoscope and the fluid management system are synergistic to each other such that both enhance the efficiency of each other. The invented system allows a body tissue cavity to be distended by continuous flow irrigation so that detached tissue pieces and waste fluid present inside a body tissue cavity are continuously automatically evacuated from the tissue cavity without causing the cavity to collapse at any stage and without the need of withdrawing the endoscope of a part of the endoscope from the tissue cavity. No type of feedback mechanism, such as mechanical or electrical, or valve or valve like systems, are incorporated in the endoscope to influence or facilitate the removal of detached tissue pieces or waste fluid in any manner.

10 Claims, 7 Drawing Sheets

(56) References Cited

U.S. PATENT DOCUMENTS

| | | |
|---|---|---|
| 5,392,765 A | 2/1995 | Muller |
| 5,441,503 A * | 8/1995 | Considine et al. ............ 606/115 |
| 5,456,689 A * | 10/1995 | Kresch et al. ................. 606/180 |
| 5,486,155 A | 1/1996 | Muller et al. |
| 5,527,331 A * | 6/1996 | Kresch et al. ................. 606/170 |
| 5,605,545 A | 2/1997 | Nowosielski et al. |
| 5,807,240 A | 9/1998 | Muller et al. |
| 6,032,673 A * | 3/2000 | Savage et al. ................. 128/898 |
| 6,110,127 A | 8/2000 | Suzuki |
| 6,113,594 A | 9/2000 | Savage |
| 6,156,049 A | 12/2000 | Lovato et al. |
| 6,645,140 B2 | 11/2003 | Brommersma |
| 6,824,544 B2 | 11/2004 | Boebel et al. |
| 7,249,602 B1 | 7/2007 | Emanuel |
| 2003/0130565 A1 | 7/2003 | Muller |
| 2003/0181906 A1 | 9/2003 | Boebel et al. |
| 2006/0041186 A1 | 2/2006 | Vancaillie |
| 2006/0047185 A1 | 3/2006 | Shener et al. |
| 2006/0122459 A1 | 6/2006 | Aue |
| 2006/0122557 A1* | 6/2006 | Kumar et al. .................... 604/67 |

* cited by examiner

SYSTEM FOR EVACUATING DETACHED TISSUE IN CONTINUOUS FLOW IRRIGATION ENDOSCOPIC PROCEDURES

The present application claims the benefit of Indian Provisional Patent Application No. 2237/DEL/2006, filed on Oct. 11, 2006, the entire disclosure of which is incorporated by reference herein.

FIELD OF THE INVENTION

The present invention relates to surgeries and, in particular, to endoscopic procedures which deploy continuous flow irrigation, such as hysteroscopic fibroid morcellation, trans uretheral prostate morcellation, hysteroscopic polyp morcellation, hysteroscopic septoplasty, hysteroscopic adhesiolysis, trans uretheral morcellation of bladder tumors, arthroscopy, and endoscopic procedures of the brain and spine.

BACKGROUND OF THE INVENTION

Continuous flow endoscopes are frequently used in endoscopic procedures such as hysteroscopy, trans uretheral urologic endoscopic procedures and arthroscopy. Those skilled in the art would know the structural composition of a continuous flow irrigation endoscope. In this application, the term "continuous flow irrigation" means that fluid simultaneously enters and escapes from a tissue cavity via separate entry and exit points, as a result of which positive fluid pressure is created inside the tissue cavity which distends the cavity. A continuous flow irrigation endoscope generally comprises an inner sheath which is placed inside the cylindrical lumen of an outer sheath. The sheaths are hollow cylindrical tubes which have a distal end which enters a tissue cavity, and a proximal end on which an inflow or outflow port is attached for the purpose of instilling or evacuating fluid from the cavity. The irrigation fluid is instilled via an inflow port.

In many prior art systems the instilled fluid travels through the lumen of the inflow sheath and enters the tissue cavity via the distal opening of the inflow sheath. The waste fluid present inside the tissue cavity enters into a potential space present between the outer and the inner sheaths via multiple holes present near the distal end of the outer sheath and this waste fluid is finally evacuated via the outflow port attached at the proximal end of the outer sheath. A fiber optic telescope is placed inside the cylindrical lumen of the inner sheath to view the interior of the tissue cavity. An endoscopic instrument can also be introduced via the lumen of the inner sheath. In this paragraph, the terms "outer sheath" and "inner sheath" refer to hollow cylindrical tubes which participate in maintaining the structural integrity of the endoscope, and such tubes also cannot move relative to each other. Also, the endoscopic instrument frequently moves relative to the outer and the inner sheaths. Various different types of "continuous flow irrigation endoscopes" have been described in U.S. Pat. Nos. 3,835,842; 5,320,091; 5,392,765; 5,807,240; and U.S. Patent Appln. Publ. Nos. 2003/0130565 A1 (Jul. 10, 2003); 2006/0041186 A1 (Feb. 23, 2006); and 2006/0122459 A1 (Jun. 8, 2006).

The arrangement described in the preceding paragraph has two major disadvantages which are negated by the system of the proposed invention. The disadvantages are as follows:

One disadvantage is that detached tissue pieces, larger than a critical size, present in the tissue cavity are unable to pass through the potential space between the outer and the inner sheaths. Thus, in endoscopic procedures the entire endoscope or the "endoscopic instrument" has to be repeatedly removed from the tissue cavity in order to evacuate the detached tissue pieces present inside the tissue cavity, and this increases the risk of complications like perforation, excessive bleeding and also increases the surgical time. As described in EP 0996375, U.S. Pat. No. 7,249,602 and U.S. Patent Appln. Publ. No. 2006/0047185, it may be argued that, instead of one outflow port, two outflow ports be installed via suitable mechanical means at suitable locations in the endoscope, one outflow port for primarily evacuating the waste fluid from the cavity and the other outflow port being meant to primarily evacuate the resected or cut tissue. However, such an arrangement is not desirable since it necessitates the incorporation of two out flow channels instead of one and it also tends to increase the overall weight of the endoscope. The system of the present invention solves all the problems described in this paragraph by utilizing only one single outflow port, attached to a single outflow channel, which serves to evacuate both detached tissue pieces and waste fluid from the tissue cavity in a continuous irrigation manner.

The other disadvantage is that the inner sheath by virtue of occupying additional space reduces the effective lumen diameter of the endoscope which necessitates a reduction in the thickness or size of the "endoscopic instrument" or the telescope or both. The system of the proposed invention reduces the problem mentioned in this paragraph by utilizing only one housing sheath and by utilizing special type of endoscopic instrument which additionally also functions as the sole outflow channel for simultaneously removing waste fluid and detached tissue pieces. In U.S. Pat. No. 6,824,544, waste fluid and tissue pieces are evacuated via an inflow sheath and the tissue is resected by a separate endoscopic instrument, loop, which cannot participate in removal of waste fluid or tissue pieces; both these features being contrary to the principals of the present invention.

Also, unlike U.S. Pat. No. 6,824,544, in the present invention, a single outflow channel (that is suction channel) is not bifurcated at the level of the endoscope and any type of valve, simple or solenoid operated, is not attached to the outflow channel. Also, unlike U.S. Pat. No. 6,824,544, in the present invention, a controller is not used for influencing or regulating the working of the endoscope, for example by way of controlling the opening and closing motion of solenoid valves. This paragraph describes requirements which essentially need to be fulfilled by the system of the present invention. These requirements have been imposed so that the use of the invented endoscope is not restricted to any specific type of fluid management system with a controller, so that only one outflow tube is needed to be connected to the endoscope, such that the endoscope is simple, light and user friendly.

In the present invention, the diameter or area of cross section of the inner lumen of a single outflow port needs to be at least equal to the diameter or area of cross section of the outflow channel, so that detached tissue pieces and waste fluid could be evacuated in the most efficient manner. Thus, in the present invention, unlike in EP 0996375, U.S. Pat. No. 7,249,602 and U.S. Patent Appln. Publ. No. 2006/0047185, a valve is not attached to the outflow channel for controlling the pressure or the fluid flow.

The present invention is essentially a continuous flow irrigation endoscope which cannot function if the single outflow channel is blocked, for example by an opening or closing valve. Thus, in the present invention, unlike in EP 0996375, U.S. Pat. No. 7,249,602 and U.S. Patent Appln. Publ. No. 2006/0047185, an opening or closing valve is not attached to the outflow channel.

The detached tissue pieces, especially the large size ones, can be evacuated by continuous flow irrigation only if the outflow channel and outflow port of the endoscope have a substantially large lumen diameter. But the same could cause the cavity to collapse intermittently during an endoscopic procedure because the "large lumen diameter" would promote the pressurized irrigation to be expelled out of the tissue cavity via a large bore outflow port. Such problem has been solved by attaching a specially designed endoscope to a specially designed fluid management system, the resultant arrangement being the system of the present invention.

OBJECT OF THE INVENTION

One object of the invention is to provide a continuous flow irrigation system, comprising an endoscope and a fluid management system, in which the detached tissue pieces and/or waste fluid present inside a tissue cavity are evacuated automatically in a continuous manner from the tissue cavity without causing the tissue cavity to collapse at any given moment of time.

Another object of the invention is to provide a continuous flow irrigation system, comprising an endoscope and a fluid management system, in which the detached tissue pieces present inside a tissue cavity are evacuated automatically in a continuous manner from the tissue cavity without the need of removing the entire endoscope or a part of the endoscope from the tissue cavity.

Another object of the invention is to provide a continuous flow irrigation system, comprising an endoscope and a fluid management system, in which both the detached tissue pieces and waste fluid are simultaneously evacuated automatically in a continuous manner from the tissue cavity via a same single outflow port connected to a single outflow channel.

Another object of the invention is to provide a continuous flow irrigation system, comprising an endoscope and a fluid management system, in which both the detached tissue pieces and waste fluid are simultaneously evacuated automatically in a continuous manner from the tissue cavity via a same single outflow port, such that no mechanical or electrical feedback mechanism or any type of valve system is utilized for evacuating the detached tissue pieces or waste fluid.

Another object of the invention is to provide a continuous flow irrigation endoscope system to which only a single outflow tube needs to be connected.

Another object of the invention is to provide a continuous flow irrigation endoscope system in which the diameter or area of cross section of the inner lumen of the outflow port is at least equal to the diameter or area of cross section of the outflow channel.

Another object of the invention is to provide a continuous flow irrigation system in which the endoscope is relatively light in weight.

Another object of the invention is to provide a continuous flow irrigation system which is user friendly, safe and efficient.

BRIEF SUMMARY OF THE INVENTION

The present invention provides a continuous flow irrigation endoscope, a fluid management system employing such an endoscope, and a method of endoscopic surgery. A continuous flow irrigation endoscope and a continuous flow irrigation fluid management system, both designed to be compatible to each other, function as a single system. The endoscope and the fluid management system are synergistic to each other such that both enhance the efficiency of each other. The invented system allows a body tissue cavity to be distended by continuous flow irrigation so that detached tissue pieces and waste fluid present inside a body tissue cavity are continuously automatically evacuated without causing the cavity to collapse at any stage, and without the need of withdrawing the endoscope of a part of the endoscope from the tissue cavity.

The endoscope has only a single housing sheath without an inner sheath.

The fluid management system comprises an inflow pump and an outflow pump (for example, an inflow peristaltic pump and an outflow peristaltic pump) which work simultaneously, for indefinite time, at fixed flow rates to create and maintain any desired cavity pressure for any desired cavity flow rate. The inflow pump is connected to an inflow port of the endoscope, while the outflow pump is connected to an outflow port of the endoscope.

DETAILED DESCRIPTION OF THE INVENTION

The system of the present invention comprises an endoscope and a fluid management system, both designed especially for each other. The endoscope and the fluid management are both based on the principles of continuous flow irrigation, as both work together as one unit to evacuate detached tissue pieces and waste fluid from a tissue cavity in endoscopic procedures which deploy continuous flow irrigation and without the necessity of withdrawing the endoscope or a part of the endoscope from the tissue cavity.

For easy understanding, the endoscope and the fluid management system shall be described separately, followed by a description of both of them together.

The Endoscope

The present invention relates to a continuous flow irrigation endoscope in which detached tissue pieces and waste fluid present inside a tissue cavity are automatically evacuated in a continuous manner without withdrawing the endoscope or any part of the endoscope from the tissue cavity.

Figure 2:
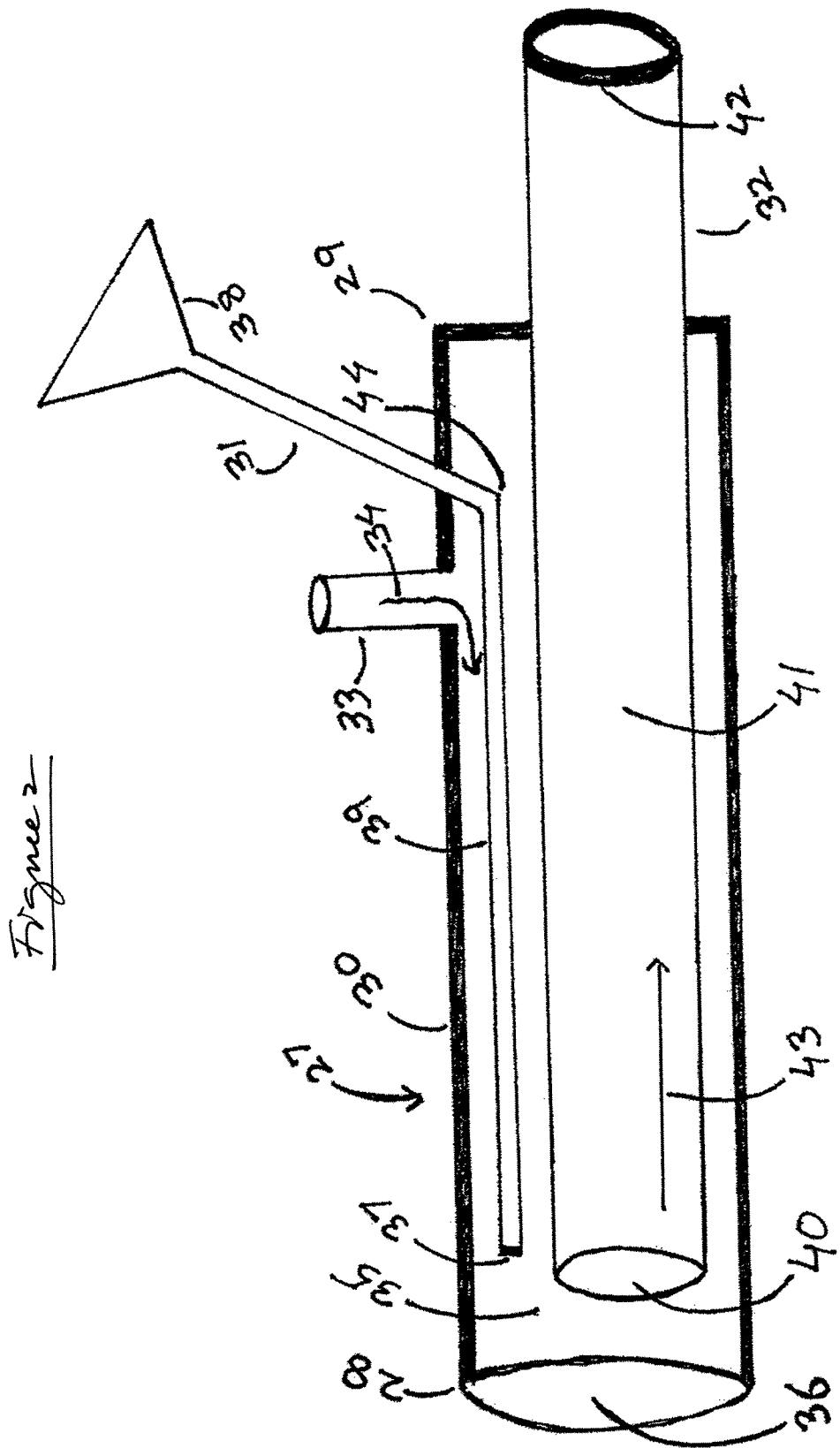
FIG. 2 shows the endoscope of FIG. 1.

The basic layout of the invented endoscope is shown in FIG. 2. The endoscope 27 has a distal end 28 which enters a tissue cavity and a proximal end 29 which lies outside the tissue cavity. The invented endoscope comprises an externally located "housing sheath" 30, an optical system 31 and a hollow cylindrical tube like instrument 32.

Again referring to FIG. 2, unlike many prior art systems, the endoscope of the present invention does not have a separate inner sheath, but rather a single sheath termed as housing sheath 30. The housing sheath 30 has an inflow port 33 located near its proximal end 29. Sterile irrigation fluid for distending a body tissue cavity is instilled via the inflow port 33 in the direction of the arrow 34. The irrigation fluid travels through the lumen 35 of the housing sheath 30 and finally enters the tissue cavity via a distally located opening 36 of the housing sheath 30. The cross section of the distally located opening 36 and/or the cross section of the housing sheath 30 could also be oval in shape, and could also have additional configurations.

Again referring to FIG. 2, a hollow cylindrical tube like instrument 32 is located inside the lumen 35 of the housing sheath 30. For brevity, the hollow cylindrical tube like instrument 32 shall be referred to as instrument 32. The instrument 32 is a hollow cylindrical tube like structure having a distal opening 40, a lumen 41 and a proximally located opening which is being termed as the outflow port 42. The lumen diameter of the outflow port 42 is the same as the lumen diameter of the rest of the instrument 32. The lumen diameter of the outflow port 42 could also be less than the lumen diameter of the rest of the instrument 32, but such an arrangement could tend to retard the evacuation of detached tissue pieces. The waste fluid and the detached tissue pieces present inside the tissue cavity enter the lumen 41 of the instrument 32 through the distal opening 40 and travel in the direction of the arrow 43. The waste fluid and the detached tissue pieces are finally evacuated via the outflow port 42. Depending upon the surgical requirement the cross section of lumen 41 could also be oval or of any other shape.

The effective cross sectional area of the housing sheath 30 should be preferably less than the effective cross sectional area of the instrument 32, as such an arrangement would facilitate the evacuation of detached tissue pieces. Here, the term "effective cross sectional area" of the housing sheath 30 relates to the total cross sectional area of the housing sheath 30 from which the cross sectional area occupied by the instrument 32 and the optical channel 39 has been subtracted. The cross sectional area of the instrument 32 is denoted by the cross sectional area of the lumen 41 of the instrument 32.

The instrument 32 is placed inside the housing sheath 30 by virtue of a fluid tight contact. Also, those skilled in the art would know that, generally, an obturator is inserted inside the housing sheath subsequent to which the housing sheath is inserted into a tissue cavity. However, the obturator assembly has not been included in the drawing only for the sake of simplicity.

Again referring to FIG. 2, the optical system 31 comprises a telescope eyepiece 38 which is connectable to a video camera, an optical channel 39 which contains fiber optic bundles and a distal viewing tip 37 for visualizing the interior of the tissue cavity. The optical channel 39 is not straight and has been deliberately provided with a bend 44. The optical channel 39 and the bend 44 are placed inside the lumen 35 of the housing sheath 30 and outside the lumen 41 of the instrument 32. In case the bend 44 is placed outside the lumen 35 of the housing sheath 30, then the fragile optical channel 39 could easily break at the bend 44. The bend 44 has been included to provide additional space for the instrument 32, especially if the instrument 32 were to be a hysteroscopic or urologic morcellator, or an arthroscopic shaver in which cases additional space is needed to accommodate the driving mechanism of the morcellator or the shaver. The optical channel could also be straight, but such an arrangement may not allow the incorporation of the said morcellator or a shaver. Also, the light source arrangement for the optical system 31 has not been included in FIG. 1 for simplicity.

Again referring to FIG. 2, the instrument 32 could be morcellator for hysteroscopic fibroid resection or for cutting a prostate adenoma in urologic endoscopic procedures. The instrument 32 could also be a shaver to be used in arthroscopic surgeries. The morcellator or the shaver have not been separately shown in any of the figures but the hollow inner channels of both are represented by the lumen 41 of the instrument 32. Also, those skilled in the art would understand that a window opening corresponding with the distal opening 40 is present near the distal end of hysteroscopic morcellators and shavers, wherein two cutting edges incorporated in two rotatable tubes facilitate tissue cutting in the region of the said window. If the window is kept in the open position while the morcellator or the shaver is not operating, then the same would allow continuous flow irrigation all through the endoscopic procedure that is even while the morcellator or shaver is non functional. The instrument 32 could also be a simple cutting knife wherein the distal end of the instrument 32 would be required to be shaped like a conventional knife. The knife could also function as a monopolar electrosurgical instrument. The instrument 32 could also be an electrode such as a ball electrode for ablating the endometrium, a prostate adenoma or a bladder tumor. The ball electrode, unlike the prior art ball electrodes, would have centrally placed a hollow cylindrical channel via which waste fluid and detached tissue generated during ablation could be evacuated.

Again referring to FIG. 2, it is important to note that instrument 32 should be essentially capable of moving in a to and fro direction relative to and parallel to the long axis of the housing sheath 30. In additional embodiments, the instrument 32 is also capable of rotating around the long axis of the instrument 32 in either direction. Suitable mechanical means are deployed to facilitate the to and fro, and the rotary, movements of the instrument 32. The distal opening 40 of the instrument 32 may also be cut obliquely such that opening 40 is oval instead of being round.

Again referring to FIG. 2, the proximal part of the instrument 32 could also be provided with a bend like the bend 44 provided in the optical channel 39, and such bend could be located inside or outside the lumen 35 of the housing sheath 30. However, such an arrangement could retard the evacuation of detached tissue pieces.

Referring to FIG. 2, the relative locations of the optical channel 39 and of the instrument 32 could even be interchanged with respect to each other or with respect to the inflow port 33.

Referring again to FIG. 2, the entire instrument 32, from the distal opening 40 to the proximally located outflow port 42, may comprise, for example, a metal, a rigid plastic material, a ceramic material, or a combination of these materials.

Also, the outlet of instrument 32 has been termed as outflow port 42 only for an easier description. In the prior art continuous flow endoscopes, the term outflow port is commonly referred to an outlet attachment which is attached at the proximal end of an outer or an inner sheath. Also, in the prior art systems the sheaths are immovable relative to each other, they do not function as an instrument, their purpose being only to provide structural integrity to the endoscope and to provide channels for instilling or removing fluid from a tissue cavity. However, in the present invention the so-called outflow port is attached at the proximal end of a movable instrument 32, the instrument not being meant to impart structural integrity to the endoscope, and the said instrument can also be replaced by a different type of instrument depending upon the surgical requirement.

Referring to FIG. 2, it is important to note that no feedback mechanism, no valves, and no valve like system have been provided anywhere in the endoscope 27 for facilitating or influencing the evacuation of detached tissue pieces and waste fluid in any manner, or otherwise. It is important to note that the proximal end of the instrument 32 has not been bifurcated in any manner. This implies that the outlet port 42 is connectable to only a single outflow tube which would transport the detached tissue pieces and the waste fluid to a waste collecting container. The outflow tube may be made of flexible resilient polymeric material. If at all any bifurcation, valve system or a feedback mechanism, as explained in this paragraph, needs to be installed then the same could be installed only in the outflow tube, sufficiently away from the endoscope 27, such that the installation does not enhance the weight of the endoscope because low weight of the endoscope is one of the objectives of the invention.

Also in the preceding paragraphs it might be misinterpreted that the instrument 32 is primarily meant to act as an outflow channel for evacuating waste fluid and detached tissue pieces from a tissue cavity. However, the primary aim of the instrument 32 is to act as an endoscopic instrument while the hollow cylindrical lumen 41 of the instrument 32 simply provides a passage for the evacuation of detached tissue pieces and waste fluid.

The outflow port 42 of endoscope 1 has a relatively large lumen diameter and the same could cause the pressurized irrigation fluid present inside the tissue cavity to be intermittently expelled via the large bore outflow port 42. This intermittently would cause the tissue cavity to intermittently collapse during an endoscopic procedure, which could lead to surgical complications like perforation and bleeding. To solve this problem, it is recommended that the endoscope 27 be used with a specially designed fluid management system which would not allow the tissue cavity to collapse and would also provide additional benefits. Such a fluid management system is described in the subsequent paragraphs.

The Fluid Management System

The fluid management system described in the subsequent paragraphs is recommended to be used with the endoscope described in the previous paragraphs. The fluid management system is a system for distending body tissue cavities in endoscopic procedures. The proposed fluid management system is meant to distend a body tissue cavity by continuous flow irrigation in such a manner that the cavity pressure is absolutely independent of the cavity outflow rate, such the both the cavity pressure and the outflow rate may be independently altered without varying the value of the other parameter. For brevity, the fluid management system shall be referred to as "system."

Figure 1:
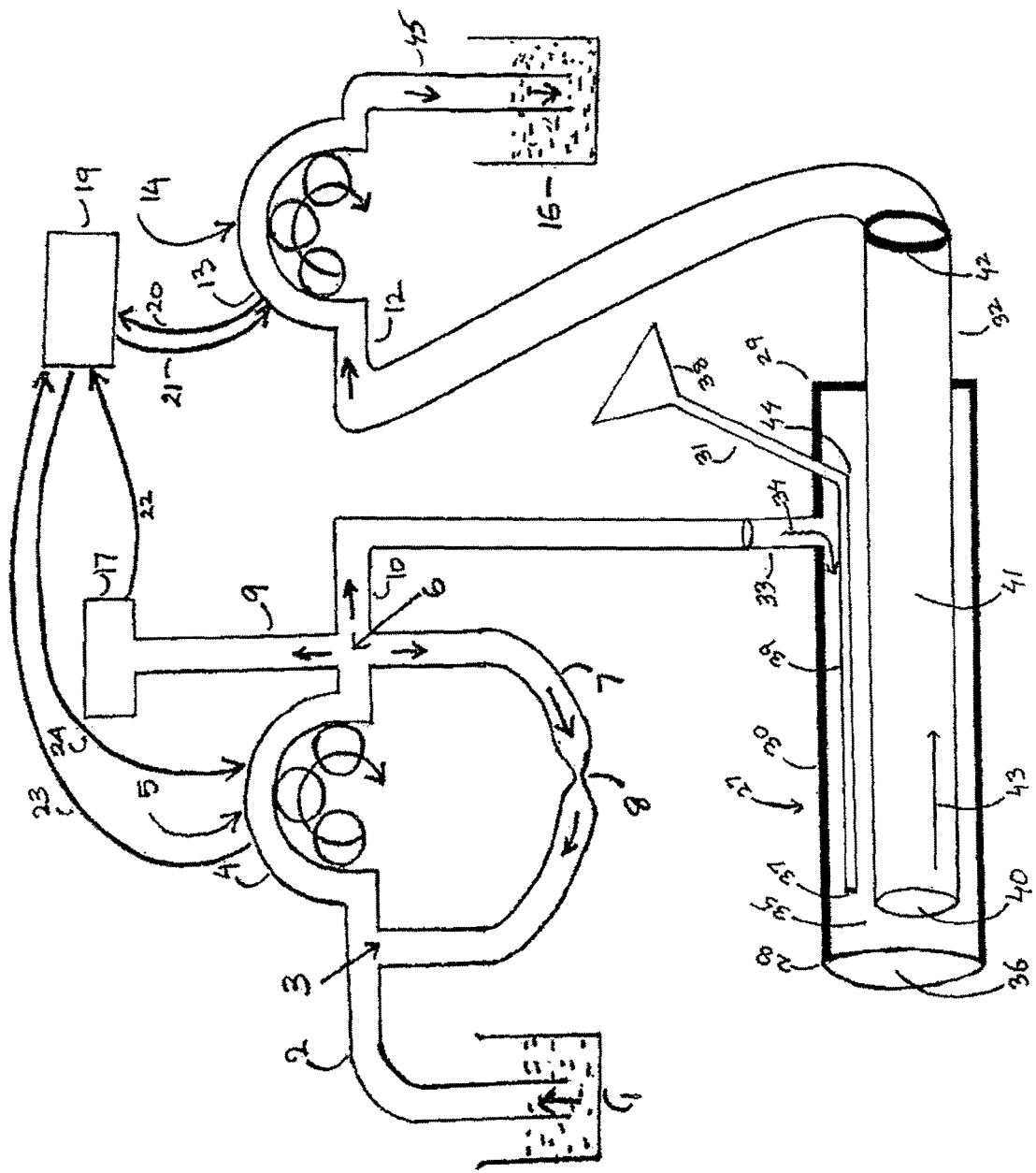
FIG. 1 illustrates an embodiment of the system of the present invention comprising an endoscope attached to a fluid management system.
Figure 3:
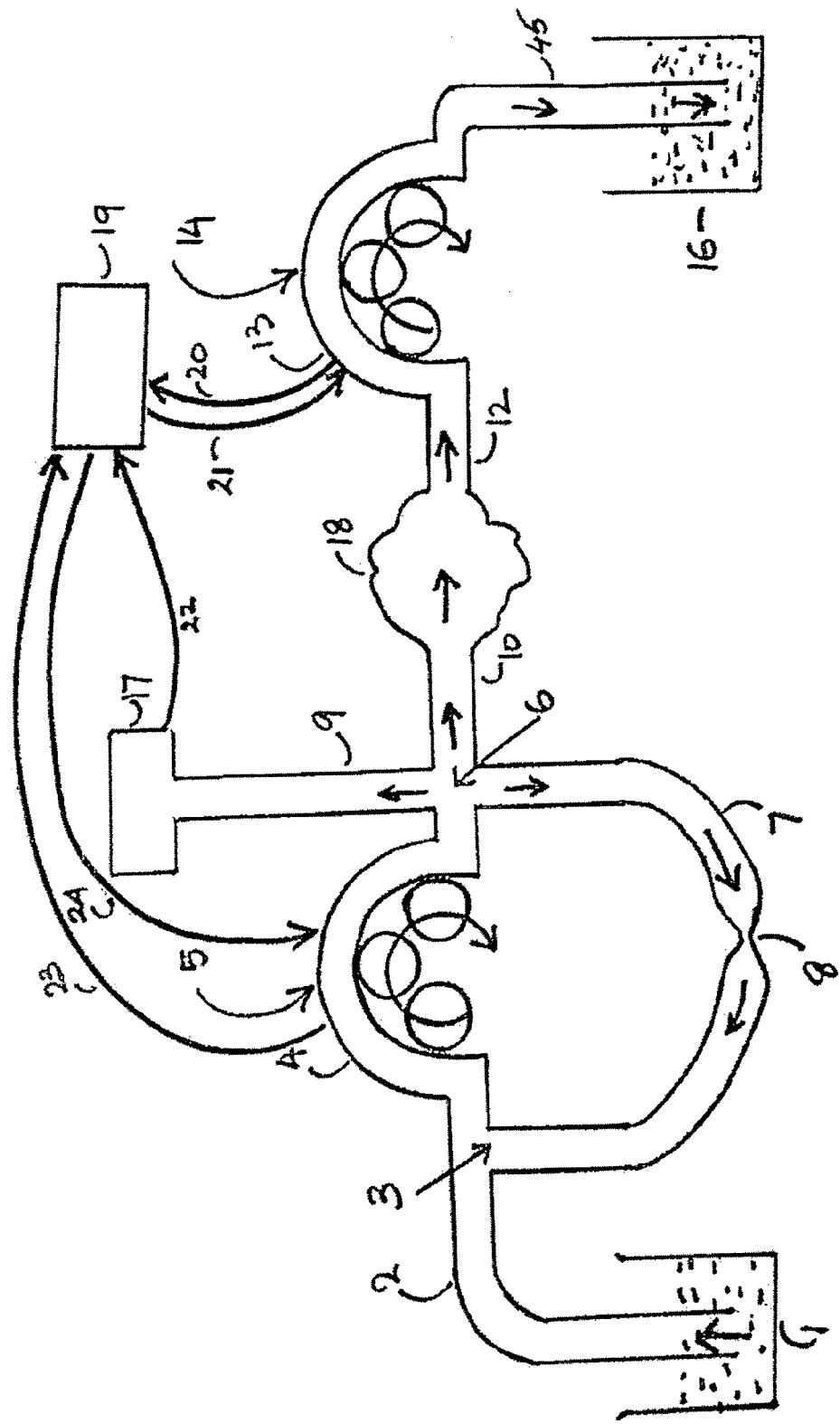
FIG. 3 is similar to FIG. 1, except that, in this figure, a tissue cavity has been substituted in place of the endoscope.
Figure 4:
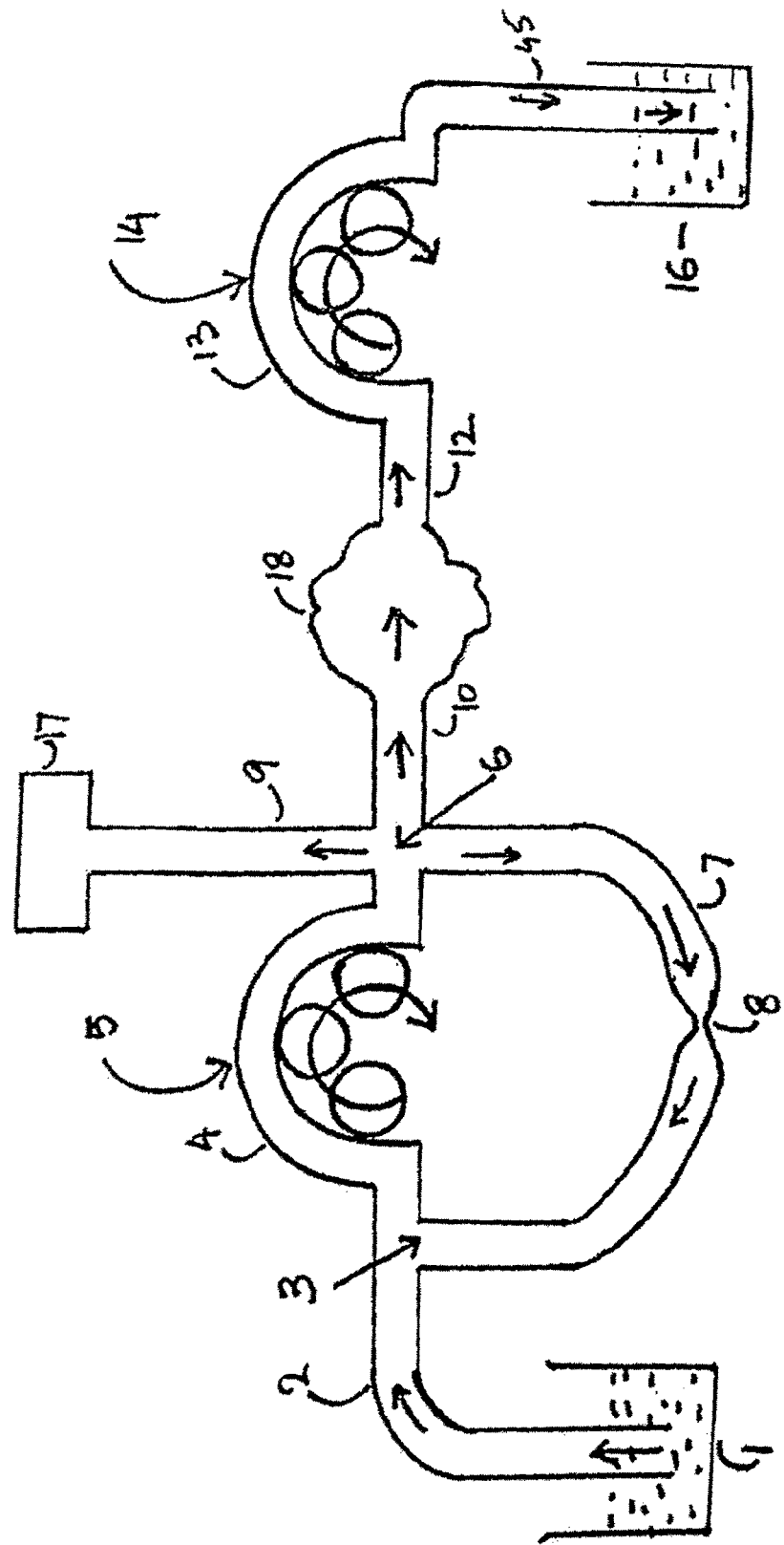
FIG. 4 is similar to FIG. 3, except that, in this figure, a controller is not included.

The schematic diagram of the system is shown in FIG. 3. Two peristaltic pumps 5 and 14 operate simultaneously to distend a tissue cavity in such a manner that the cavity pressure is totally independent of the cavity outflow rate. FIG. 3 represents the complete schematic diagram of the "system." Please note that the controller being used in the system shown in FIG. 1 is an optional feature and the system would provide most of the features even without the controller. FIG. 4 represents the schematic diagram of the system but without a controller system. Thus, FIG. 4 is a mechanical version of the system. An operator, for example, a human operator, is required to operate such mechanical version of the system shown in FIG. 4. Though it is recommended that the controller based version of the system be used in endoscopic surgeries, it is not essential. The controller being used in the present system merely assists the user in arriving easily at some of the additional functions which otherwise can be performed manually. Thus, in this application, the mechanical version of the system shown in FIG. 4 is discussed in more detail to explain the basic physical principles of the system with greater clarity.

Referring to FIG. 4, the system shown in this figure comprises two peristaltic pumps which can maintain a predictably precise stable cavity pressure for indefinite time by working simultaneously at constant rotational speeds. Pump 5 pushes fluid into the cavity 18 and while pump 14 simultaneously extracts fluid out of the cavity 18. The inlet end of the inflow peristaltic pump 5 is connected to a fluid source reservoir 1 via tube 2. The distal open end of tube 2 is constantly submerged in a sterile non viscous physiological fluid like 0.9% normal saline, 1.5% glycine, ringer lactate or 5% dextrose contained inside the reservoir 1 at atmospheric pressure. One end of the tube 7 connects the "T junction" 3 situated at the inlet end of the pump 5 while the other end of tube 7 connects with the square junction 6 situated at the outlet end of the pump 5. The T junction 3 is thus the meeting point of three tubes, namely 2, 4 and 7. Similarly, the square junction 6 is the meeting point of four tubes 4, 9, 7 and 10. The rollers of the peristaltic pump 5 continuously compress and roll over the entire length of tube 4 thus displacing fluid in the direction of the curved arrow. This curved arrow denotes the direction in which the rotors of the peristaltic pump 5 rotate.

Tube 7 has a constriction point 8 which can be located anywhere along its length. Such constriction point refers to a point where the inner diameter of the lumen of tube 7 is reduced in comparison to the lumen of the rest of the tube 7. Such constriction may be a permanent constriction in the lumen of tube 7 or it may be a variable constriction whose diameter may be increased or decreased as desired. A pressure transducer 17 is attached at one of tube 9 while the other end of tube 9 is connected anywhere on inflow tube 10. For practical convenience it is desirable that the other end of tube 9 be connected in the up stream part of the inflow tube 10 such as at the square junction 6. The pressure transducer 17 measures the fluid pressure via a column of liquid or air present in the lumen of tube 9. The fluid pressure as measured by the pressure transducer shall be referred to as P. In this application, the term "P" shall frequently be used to refer to the actual pressure inside the tissue cavity but in physical terms P is the pressure sensed by the transducer 17 at point 6. The pressure transducer 17 may also be in the form of a membrane diaphragm incorporated in the wall of the inflow tube 10 such that this membrane diaphragm is in direct contact with the fluid contained in the inflow tube 10, such that the linear movement excursions of the said membrane are interpreted as pressure of the fluid inside the inflow tube 10 by a suitable pressure transducer. Such type of pressure sensor being directly incorporated in the wall of the inflow tube 10 senses the fluid pressure without the intervention of tube 9. The basic purpose of the transducer is to measure the fluid pressure inside the inflow tube 10, such as at point 6, thus the mechanical construction of the transducer is not important as long as it measures the fluid pressure. For simplicity, the existence of tube 9 shall be continued to be considered in the rest of the application. The peristaltic pump 14 attached to the outflow side actively extracts fluid out of the tissue cavity 18 via the out flow tube 12. The outlet end of the pump 14 is connected to a waste fluid carrying tube 45 which opens into a waste fluid collecting reservoir 16 at atmospheric pressure. The rollers of the pump 14 constantly compress and roll over the entire length of the peristaltic pump tubing 13, thus displacing fluid in the direction of the curved arrow which also corresponds with the direction of pump rotation.

To understand the system in a simpler manner, both pumps are being considered to be identical in all respects and all the tubes are also being considered to be having the same uniform inner diameter. However, the inner diameter of the tubes could also be different. Tubes 4 and 13 consist of a soft resilient plastic material which can be efficiently compressed by the rollers of the peristaltic pumps. The other tubes also consist of a suitable resilient plastic material. It is assumed that all the components shown in FIG. 4, including the two pumps, all tubes and the cavity, are placed at the same horizontal height with respect to the ground. Also, the rollers of pumps 5 and 14 should press adequately over tubes 4 and 13 so that there is no leak through these tubes when the pumps are stationary. It is also assumed that there is no abnormal leak of fluid in the irrigation system, for example leak via a accidental hole made in any irrigation tube or a fluid leak which might occur if the endoscope loosely enters into the tissue cavity (for example, in hysteroscopic surgery, fluid leaks by the sides of the endoscope if the cervix is over dilated).

Figure 7:
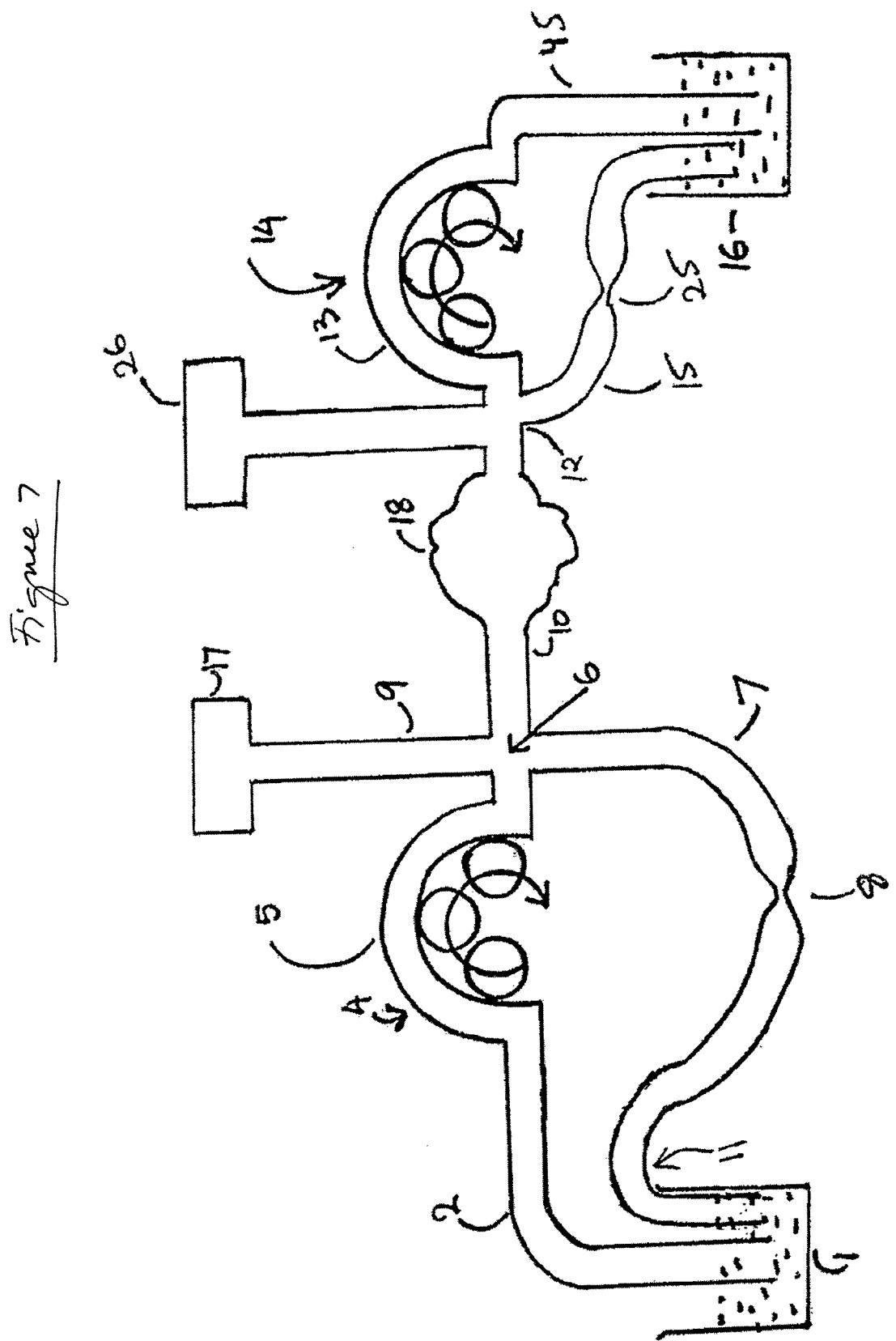
FIG. 7 is similar to FIG. 2, except that, in this figure, an additional/optional constriction site housing tube 15 and an additional/optional pressure transducer 26 have been included.

One end of the constriction site housing tube 7 instead of being connected with tube 2 at the T junction 3 can also open directly into the fluid source reservoir 1. This shall not affect the efficiency of the system in any way but it may be practically difficult from the surgical point of view in some special cases. Thus, such a provision is separately shown in FIG. 7 and the tube has been labeled as 11 but it has intentionally not been included in the main block diagram of the system in FIGS. 3 and 4 to keep the drawings simple. Also, a constriction site housing tube similar to tube 7 labeled as 15 can be attached to the outflow tube 12 as shown in FIG. 7. In tube 15, the constriction site is labeled as 25. Such tube can serve a number of purposes. Tube 15 can be utilized for relatively faster evacuation of air bubbles from the cavity. In place of the adjustable constriction site 25, a pressure release safety valve may be incorporated as a safety feature, however it is more beneficial to install such pressure safety valve in the inflow circuit. The tube 15 may also be used for quickly flushing air bubbles from the irrigation tubes by fully opening the constriction site 25 for a few minutes or seconds. The tube 15 may also be used for any other purpose as deemed fit by the surgeon. However, tube 15 has intentionally not been included in the main block diagrams of the system because by including the tube 15 in the main block diagrams it would have become very difficult to explain the basic physical principals of the system. However, tube 15 is a very beneficial component and is thus recommended to be incorporated in the system. The opening and closing of the constriction site 25 can also be regulated manually to help in various special advanced endoscopic applications. Incorporation of tube 15 with the variable constriction site 25 can help in reducing the substantially high amplitude pressure variations inside the cavity caused by abnormally large cavity wall contractions, but such phenomenon is only rarely encountered. Also, an additional pressure transducer 26 may also be attached on the out flow tube 12, if desired, as shown in FIG. 7. However, the pressure transducer 26 has intentionally not been included in the main block diagrams of the system because, by doing so, it would be very difficult to explain the basic physical principles of the system.

Figure 5:
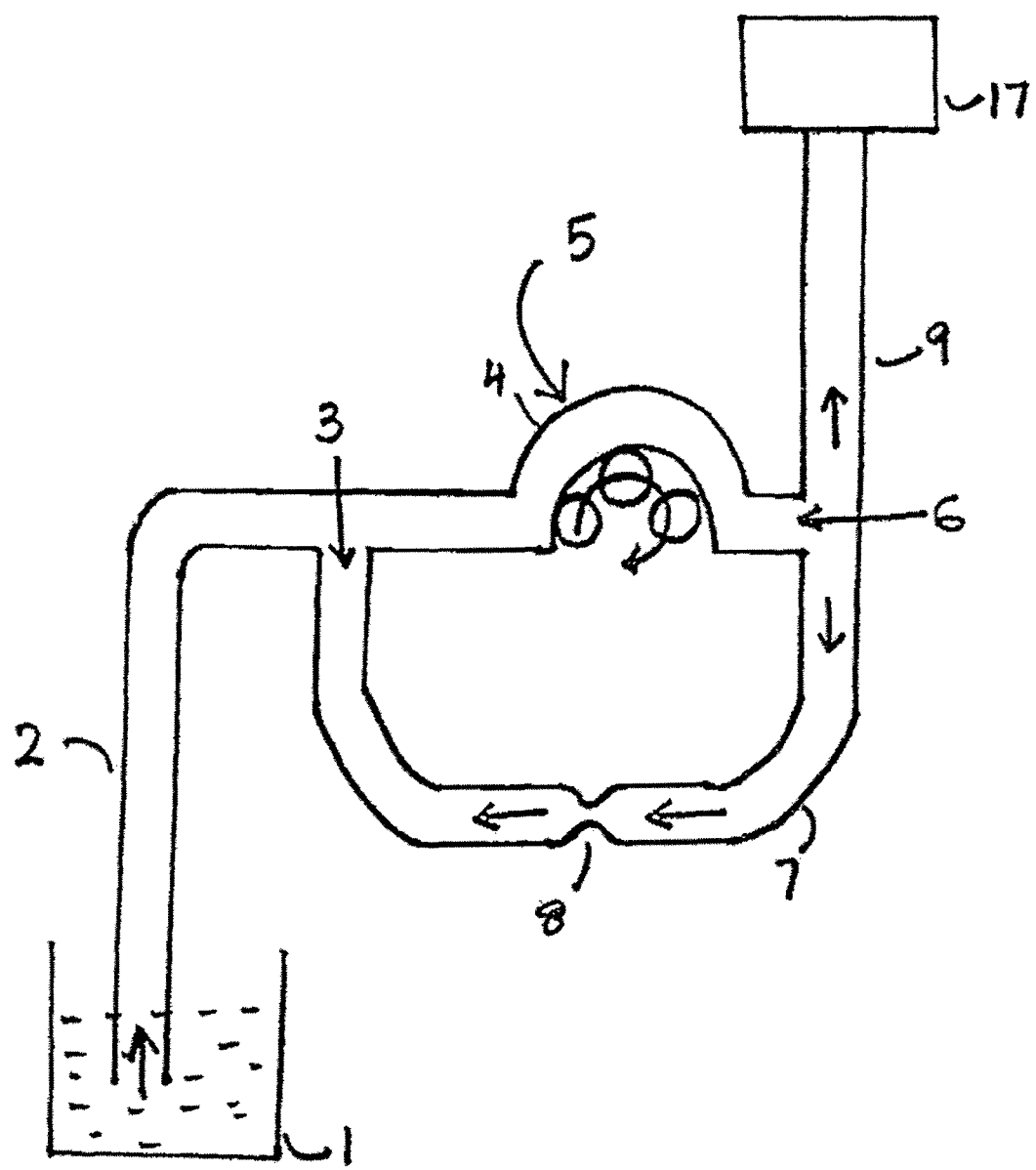
FIG. 5 shows the inflow part of the fluid management system along with the inflow peristaltic pump 5, the pressure transducer 17 and the constriction site 8.

To clearly understand the system shown in FIG. 4, it is helpful to discuss the functioning of the inflow peristaltic pump 5 as a separate entity as shown in FIG. 5. The rollers of pump 5 move in the direction of the curved arrow and squeeze over the entire length of peristaltic pump tubing 4. Initially, tubes 2, 4, 7 and 9 contain air at atmospheric pressure and the free open end of tube 2 is submerged in a sterile fluid contained inside the fluid source reservoir 1. The moment the constriction site 8 is fully occluded, a column of fluid is immediately sucked into tube 4 via tube 2, and thus fluid starts accumulating in the proximal parts of tubes 9 and 7. As the fluid fills in, tube 9 it pushes a column of air distal to the fluid column created in tube 9 and the pressure of this compressed air column is sensed by the pressure transducer 17. The fluid pressure and the pressure of the compressed air column are same, thus the pressure transducer 17 actually senses the fluid pressure. If tube 7 continues to remain fully occluded at the constriction site 8, the fluid continues to accumulate inside tubes 9 and in that part of tube 7 which lies between point 6 and the constriction site 8, and the pressure transducer 17 thus displays a continuously rising fluid pressure. The moment the block at the constriction site 8 is partially released, the fluid escapes in the form of a jet through the partially open constriction opening 8 in the direction of point 3. With the constriction opening 8 being only partially blocked, if the pump 5 continues to rotate at a constant rotational speed, the fluid pressure ultimately gets stabilized at a fixed value provided the internal diameter of the constriction site 8 is not further varied. The diameter D of the constriction site 8 ranges from a minimum non-zero value to a maximum value which is less than the overall diameter of the rest of the housing tube. Thus, in this application, the inner diameter of the constriction site 8 shall be deemed to be fixed at some predetermined value D, unless otherwise stated. The fluid being displaced by the peristaltic pumps is actually pulsatile in nature, thus the fluid pressure exhibits minute pulsations having a fixed frequency and a fixed amplitude. From a practical point of view, such minute pressure fluctuations of such a regular nature can be ignored in context with distension of body tissue cavities in endoscopic procedures. Thus, in the entire application, the fluid pressure shall be assumed to be non-fluctuating in nature.

Figure 6:
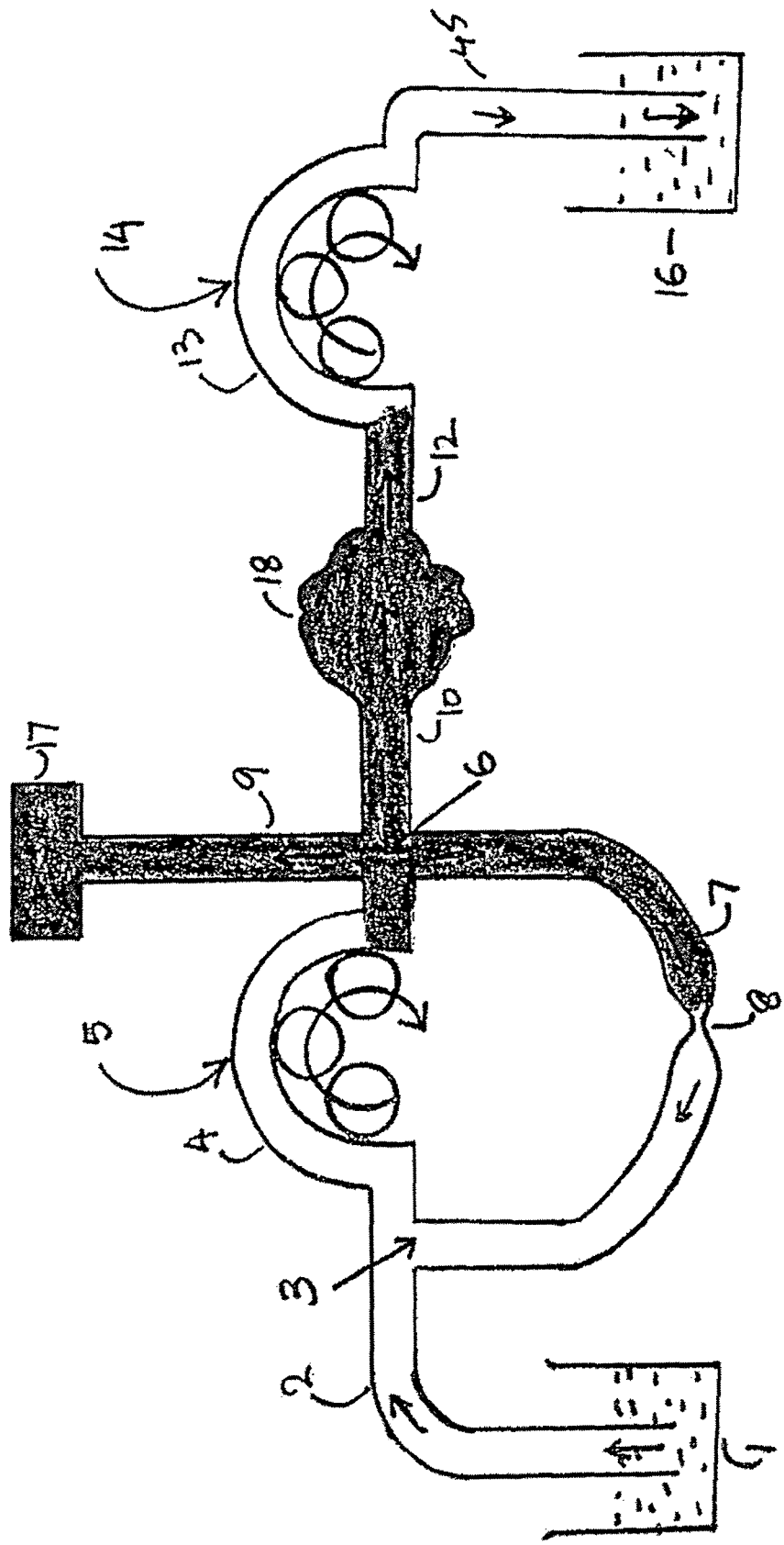
FIG. 6 is similar to FIG. 4, except that, in this figure, a shaded area represents a region having an almost similar pressure.

Referring to FIG. 6, this figure is similar to FIG. 4 but a limited region of the irrigation circuit having an almost same pressure has been shaded black. Due to frictional resistance experienced by the moving fluid the pressure at point 6, as sensed by the transducer 17, is always found to be higher than the actual pressure inside the tissue cavity 18 but the pressure difference is so small that it may be neglected from the practical surgical point of view. Also, such pressure difference increases as the fluid flow rate increases. The term "out flow rate" refers to the flow rate of pump 14. Also, the pressure difference remains constant all through surgery at any fixed outflow rate. Though the pressure difference is negligible, if desired, its effect can also be totally negated by subtracting its value from the pressure reading of the transducer. In this manner, in endoscopic surgeries, it is possible to determine the actual cavity pressure by using the pressure transducer 17 located far away from the cavity. This feature is of special relevance because, in endoscopic procedures like hysteroscopy, arthroscopy and brain endoscopic surgery, it is important to know the actual cavity pressure but at the same time it is practically difficult to take a pressure measurement directly from the cavity.

Referring to FIG. 4, it shall be first described as to how the system can be used mechanically, that is without a controller. The peristaltic pumps 5 and 14 can be made to work at any fixed rotational speed and the fluid flow rate of each pump is directly proportional to the pump RPM or the pump rotational speed. Thus, any precise pump flow rate can be generated by selecting a suitable pump rotational speed. The fluid flow rate of pump 14 shall henceforth be denoted by R2 and shall be termed as the "outflow rate." The fluid flow rate of pump 5 shall be denoted by R1 and shall be termed as the "inflow rate." Here, it is to be noted that the term "inflow rate" R1 is not the true inflow rate for the cavity 18, as might be suggested by the literary meaning of the term "inflow" because R1 is not the actual rate at which fluid into the cavity 18 because some fluid also constantly escapes through the constriction site opening 8. Thus, the term "inflow rate" refers to the flow rate of the inflow pump 5 unless specifically mentioned. However, the term "outflow rate" R2 does correspond to the literary meaning of the term "outflow" because R2 is equal to the rate at which fluid flows out of the cavity 18. The surgeon initially decides an outflow rate R2 by selecting a suitable rotational speed for pump 14. Next, the surgeon decides the maximum flow rate at which fluid could be allowed to enter into the cavity via the inflow tube 10 and the inflow pump 5 is set to work at such flow rate or at a flow rate slightly lesser than this. Intravasation is the process by which fluid enters into the patient's blood circulation through the cut ends of blood vessels located in the cavity wall or enters into the patient's body, for example into the peritoneal cavity, as a result of an accidental perforation or escapes via patent fallopian tubes into the peritoneal cavity. Thus, "intravasation" is a process by which the pressurized irrigation fluid enters into the patient's body system through the walls of the tissue cavity. In case of a surgical accident, like cavity wall perforation, the fluid being pumped by the inflow pump 5 can enter into the patient's body at a rate almost equal to R1. It is obvious that the maximum rate of fluid intravasation cannot exceed the value R1. In case of an accident, like cavity wall perforation, it may take some time before an abnormally high intravasation rate is discovered and in such time a dangerous quantity of fluid might enter into the patient's body. If the inflow rate R1 is kept at a relatively lower value then the volume of intravasated fluid in case of such an accident would be low. After fixing the values for R2 and R1, the system is started and the diameter of the constriction site 8 is gradually reduced. As the diameter of the constriction site 8 is reduced, fluid starts flowing into the tissue cavity and the pressure inside the tissue cavity starts rising. When the desired pressure is achieved inside the tissue cavity, the diameter of the constriction site 8 is not reduced any further and is fixed. The diameter of the constrictions site at this stage is termed as "D". The constriction site may also be a plastic or metal piece which has a hole in the centre such that the diameter of the hole is permanently fixed at some value D. If a constriction 8 has a permanently fixed diameter then only the flow rates of pumps 14 and 5 have to be set before the system becomes completely operational.

The inventors here would like to discuss the importance of incorporating the housing tube 7 with the constriction site and the non-obvious advantages provided by the housing tube 7 with the constriction site.

The surgeons have only two options, either to ignore cavity pressure variations by not correcting them, or to externally and actively correct such pressure variations. To externally and actively correct the variations in the cavity pressure, a controller is generally incorporated and the working of the pumps is essentially controlled by the controller. Incorporation of the controller controlling the operation of the pumps does not provide any benefit. The controller activates the controlling action after the variations in the cavity pressure have subdued. Thus, the controlling action initiated by the controller instead of benefiting the surgeon leads to an undesirable turbulence inside the cavity and also tends to amplify the resultant movement excursions of the cavity walls.

The inventors have noticed that if the controller continuously controls the operations of the pumps (either on the inflow side or on the outflow side), the cavity pressure continuously fluctuates around a preset value and it is not possible to attain a constant value. The Inventors believe that the controller provides proper corrective action (by continuously controlling the operations of the pumps) only if the fluctuations in the cavity pressure are gradual and not highly instantaneous. That is, if the quantitative rise/fall in the cavity pressure is over long time period, the controller would be able to provide proper corrective action. As the time period to detect variation in the cavity pressure and commence corrective action is ideally in the range of 2 to 4 seconds, if the quantitative rise/fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus, it takes very long time period for the system to once again get stabilized.

The inventors have surprisingly found that incorporation of a housing tube provided with a constriction site at the inflow side as described above inherently and passively corrects the pressure variations due to physiological cavity wall contractions and the mechanical movement of the tubes and the endoscope, and also limits the variation in the size of the cavity. The applicants highlight that it is important to control both the variations in the pressure inside the cavity and the changes in the size of the distended cavity. Large variations in the pressure inside the cavity or the size of the cavity are detrimental to the surgical procedure. During the contraction of the cavity, a minute quantity of the fluid is pushed out of the cavity. If during this stage the system does not provide a way for releasing the fluid being pushed out, the instantaneous pressure inside the cavity increases tremendously which is harmful to the patient. On the other hand, if the amount of fluid being pushed out of the cavity is not checked or controlled, the changes in the size of the distended cavity are very high. The incorporation of the housing tube having the constriction site in the present system controls both the variations in the pressure inside the cavity and the changes in the size of the distended cavity. The housing tube having the constriction site provides a by-pass route for the fluid being pushed out of the cavity to go back to the fluid supply tube or the fluid source reservoir. This avoids the instantaneous pressure surge inside the cavity which is harmful to the patient. The size of the diameter at the constriction site automatically controls the amount of fluid passing through the housing tube, thereby controlling the amount of fluid being pushed out of the cavity. Inclusion of the housing tube with the constriction site therefore minimizes the instantaneous variations in the size of the distended cavity.

Alternatively, if the cavity expands, a suitable volume of fluid is sucked into the cavity from the irrigation circuit, such as from the region of point 6. This is accompanied by a corresponding transient decrease in the flow rate at which fluid which fluid is escaping via the constriction site 8 in the direction of point 3 but if the magnitude of the physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8.

Determining the Real Time Rate of Fluid Intravasation

Referring to FIG. 4, let it be hypothetically assumed that the diameter at the constriction site 8 has been fixed at some predetermined value D, the outflow and the inflow rates have been fixed at some values R2 and R1 respectively and in such a situation a pressure P is created inside the tissue cavity 18 when the system is operated. In such case, if no intravasation occurs during the endoscopic procedure then the pressure inside the tissue cavity 18 continues to remain at the same value P. However, if at any stage during the endoscopic procedure intravasation occurs, then the cavity pressure immediately falls below the desired initial value P and inflow rate has to be increased by some magnitude in order to raise the cavity pressure to its initial value P. Here, magnitude of the required increase in the inflow rate to attain the initial cavity pressure P is equal to the instantaneous real time rate of intravasation R3 existing at that moment of time. In this way, the real time rate of fluid intravasation can be determined by using the mechanical version of the system.

Cavity Pressure or the Outflow Rate, Both can be Altered Independently without Varying the Value of the Other Parameter Referring again to FIG. 4, a hypothetical endoscopic procedure is being considered where surgery is being performed at an outflow rate R2 and inflow rate R1 with the constriction 8 diameter being been fixed at some value D and a resultant cavity pressure P being created maintained. In such hypothetical situation, as long as R2 and R1 are not altered, the cavity pressure P remains predictably constant throughout surgery resulting in a predictably stable mechanical distension of the tissue cavity walls which culminates in constant clear visualization throughout the endoscopic procedure. If in the hypothetical procedure the cavity pressure needs to be increased without altering the out flow rate R2, then all that is needed is to start increasing the value of R1 and stop doing so when the desired higher cavity pressure is achieved. Similarly, if the cavity pressure needs to be decreased without altering the out flow rate R2 then R1 is decreased till the desired lower cavity pressure is attained. In the hypothetical endoscopic procedure, if the outflow rate R2 needs to be increased without altering the cavity pressure P, then the value of R2 is increased by the desired magnitude but simultaneously the value of R1 is also increased by a similar magnitude. Similarly, if the outflow rate R2 needs to be decreased without altering the cavity pressure P, then the value of R2 is decreased by the desired magnitude but simultaneously the value of R1 is also decreased by a similar magnitude. Thus, if R1 and R2 are simultaneously increased or decreased by the same magnitude the cavity pressure does not vary, and the value D is always fixed as already stated.

The preceding statements shall now be explained by the help of a numerical hypothetical example. In reference to FIG. 4, considering a hypothetical situation in which an endoscopic procedure is being done at an outflow rate of 100 ml/minute, an inflow rate R1 and the cavity pressure being 80 mm Hg. If the surgeon wants to increase the outflow rate to 322 ml/minute by maintaining the cavity pressure at the same value of 80 mm Hg, the outflow rate is increased to 322 ml/minute and the inflow rate is increased by 222 ml/minute, because 322 ml/min−100 ml/min=222 ml/minute. As already mentioned, if both inflow and outflow rates are increased or decreased by the same magnitude, the cavity pressure does not change. Thus, the final inflow rate becomes R1+222 ml/minute, where R1 was the initial inflow rate. Thus, in the proposed system of the present invention, the cavity pressure and the outflow rate both can be altered absolutely independent of each other without affecting the value of the other parameter.

Mechanical Version of the System

The mechanical version of the system shown in FIG. 4 can be used practically in endoscopic surgeries but it requires a human operator. Thus, the controller based version of the system shall be discussed in subsequent paragraphs.

Controller Based Version of the System

Referring to FIG. 3, this figure shows a schematic diagram of the system with a controller. FIG. 3 and FIG. 4 are similar except that in FIG. 4 the controller system is not included. A tachometer, not shown in the diagrams, is coupled to each peristaltic pump and sends information regarding the pump rotation speed to the controller 19 via wires 20 and 23. The pump flow rates being proportional to the pump rotation speed, the tachometer signal always conveys flow rate related information to the controller. As already mentioned, both peristaltic pumps have been considered to be similar in all respects because this makes it easier to understand and operate the system. However, the two peristaltic pumps may also be different in context with the inner diameter of the peristaltic pump tubes 4 and 13 but in such case suitable modifications have to be made in the controller programming in order to operate the system as described in this manuscript. The controller also regulates the rotation speed of the two pumps via electrical signals sent through wires 24 and 21. The pressure transducer 17 conveys the pressure signal to the controller via wires 22. On the basis of a pressure feed back signal received from the pressure transducer 17 the controller regulates the rotational speed of the inflow pump 5. The outflow pump 14 works at fixed outflow rates and the flow rate of this pump is also regulated by the controller via suitable electrical signals sent via wires 21. A provision exists by which desired values for P and R2 can be fed into the controller and the values R1, R2 and P can be continuously displayed via suitable display means incorporated in the controller. The controller can be programmed to perform many special functions related to endoscopic surgery which shall be discussed in the following paragraphs.

Method of Operating the Controller Based Version of the System

Referring to FIG. 3, in context with the system at the start of surgery the surgeon initially selects suitable values for cavity pressure P and outflow rate R2. The desired values of P and R2 are fed into the controller via suitable input means incorporated in the controller. The diameter D at the constriction site 8 remains fixed at some pre selected value. The diameter of the constriction site 8 is so chosen that it suits the operational needs of the endoscopic procedure. The method of selecting a suitable diameter D for the constriction site 8 has already been discussed under the heading "Selection of a suitable diameter for the constriction site." When the system shown in FIG. 3 is operated, the controller 19 instructs the outflow pump 14 via wires 21 to continuously extract fluid out of the body cavity 18 at a desired fixed outflow rate R2. Thus, all through the surgery, the outflow rate remains fixed at R2 irrespective of any internal or external factors unless intentionally changed by the surgeon. The cavity pressure is sensed by the pressure transducer 17 and a corresponding pressure feedback signal is sent to the controller via wires 22 on the basis of which the controller regulates the inflow rate R1, via wires 24. After the system is made operational the controller 19 gradually increases the inflow rate up to the point where the desired preset cavity pressure P is achieved. Let the value of the inflow rate at which the desired cavity pressure is achieved be termed as "R1. final." It is obvious that the value "R1.final" is actually determined by the controller by a pressure feed back mechanism and such determination of the value is based on the preset values of R2 and P. The controller is so programmed that once the value "R1.final" is achieved and is maintained for a desired minimum time interval, for example 10 seconds, after which the controller releases the inflow pump 4 from its pressure feedback control mechanism and allow the inflow pump 4 to operate on its own at an inflow rate "R1.final" which was determined by the controller. In this manner, the two peristaltic pumps continue to work at fixed flow rates to maintain a desired stable cavity pressure. The controller is also programmed that in case the cavity pressure subsequently alters, for example due to intravasation, by a desired minimum preset magnitude and for a desired minimum time, which may hypothetically be 10 seconds, the inflow pump 4 again comes under the pressure feedback control of the controller and a new value of "R1.final" is determined by the controller after which the inflow pump 4 is again allowed to be operated without the pressure feedback mechanism at the newly determined "R1.final" inflow rate. Such sequences of events continue to occur throughout the endoscopic procedure. Taking an imaginary example, if the total surgical time is 60 minutes then it may be hypothetically possible to operate the inflow pump independent of the pressure feedback mechanism for 55 minutes and under the control of the pressure feedback mechanism for 5 minutes. However, provision of operating the inflow pump 4 under a pressure feedback mechanism all through the endoscopic procedure can also be incorporated.

The Advantage of Operating the Inflow Pump Independent of the Pressure Feedback Mechanism One reason for operating the inflow pump 4 independent of the pressure feedback mechanism is to avoid unnecessary corrections of minor pressure variations caused by physiological cavity wall contractions. In the present system, the physiological variations in cavity pressure are automatically corrected by the constriction site 8 without the need of a controller. If the cavity contracts a minute quantity of fluid which is pushed out of the cavity escapes via the constriction site 8 towards point 3. It is noted that the part of tube 7 between point 8 and 3 is at atmospheric pressure, thus the fluid which is expelled from the cavity as a result of a physiological contraction escapes through the constriction site 8 against a zero pressure head, which is atmospheric pressure. Thus, the transient, insignificant and instantaneous rise and fall in cavity pressure gets stabilized at the desired preset value within a fraction of seconds. Alternatively, if the cavity expands a suitable volume of fluid is sucked into the cavity from the irrigation circuit, such as from the region of point 6, and this is accompanied by a corresponding transient decrease in the flow rate at which fluid is escaping via the constriction site 8 in the direction of point 3 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8. Normally, the direction of such imaginary vector is always towards point 6 while its magnitude constantly varies to take care of the pressure changes resulting due to physiological cavity contractions. Normally, a cavity continuously contracts and dilates by approximately the same magnitudes, thus there is no logic to check the minor pressure variations emanating from the said contractions. Also, the opening of the constriction site 8 does not allow the said physiological cavity pressure fluctuations to cause any significant cavity wall movement excursions by allowing to and fro movement of flow through its lumen. However, if the pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller. As already explained, the controller is so programmed that the inflow pump 4 automatically comes under the pressure feedback control mechanism of the controller in case the cavity pressure alters by a desired minimum preset magnitude and for a desired preset time interval, thus a new "R1.final" inflow rate is established at which the inflow pump is again allowed to operate without the feedback control of the controller. As a safety precaution, a provision can be made in the controller via suitable input means to fix an upper safe limit for the inflow rate R1 and the cavity pressure P such that these safe limits are not exceeded accidentally.

Controller Programming for Determining the Instantaneous Rate of Fluid Intravasation During Surgery In the above paragraphs a mechanical method of determining the instantaneous real time instantaneous rate of fluid intravasation without using the controller has been described. However, such mechanical evaluation is subject to human error and is also difficult to repeat multiple times during an endoscopic procedure. Hence, the need arises to continuously determine and display the real time rate of fluid intravasation by the help of the controller. Excess fluid intravasation during an endoscopic procedure can even lead to the patient's death thus it is extremely important for the surgeon to reliably, accurately and constantly know the real time rate of fluid intravasation R3 throughout the endoscopic procedure. In order to determine the real time rate of intravasation, an equation $KP=(R1-(R2+R3))^2$ has been derived where K=constant, P=cavity pressure, R1=inflow rate, R2=outflow rate and R3=instantaneous rate of fluid intravasation. In the equation, the values of P, R1 and R2 are always known by the controller and the value of the constant K can be determined by suitable analytical means. Thus, in the equation, R3 is the only unknown value which can be determined by feeding the expression contained in the equation into the controller via suitable programming means and directing the controller to continuously determine and display R3. The controller can be further programmed to carry out multiple other functions related to intravasation, such as an alarm being sounded if intravasation of a specific minimum magnitude occurs or if the rate of intravasation rate increases by a specific magnitude. The controller can also be programmed to completely shut down the system in case the rate of intravasation exceeds a specified dangerously high rate.

Selection of a Suitable Diameter for the Constriction Site

If the diameter of the constriction site 8 is very small, then the transient pressure fluctuation in the cavity pressure would be of a relatively larger magnitude and would last for a relatively longer time interval but the associated resultant movement excursion of the cavity wall would be of a relatively small amplitude. Similarly, if the diameter of the constriction site 8 is very large, then the transient cavity pressure fluctuations would be of a relatively smaller magnitude and would last for a relatively shorter time interval, but the associated resultant movement excursion of the cavity walls would be of much larger amplitude. These statements are explained by the help of three hypothetical numerical assumptions as stated in table 1 which is as follows:

TABLE 1

| Serial number of the assumption | A hypothetically assumed numerical value of the constriction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.1 mm | 20 mm Hg | 3 seconds | 0.5 mm |
| 2 | 1 mm | 5 mm Hg | 1 second | 1 mm |
| 3 | 1.5 mm | 1 mm Hg | 0.5 seconds | 5 mm Hg |

(*Note: A similar table can be hypothetically constructed taking into consideration cavity wall expansion, instead of contraction.)

In context of routine endoscopic procedures, the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus, the nuisance value of a cavity wall movement excursion is relatively more than the nuisance value of the said transient pressure surge. However, the amplitude of the pressure surge should also be not very high because it may promote intravasation and other problems.

Thus, while selecting the diameter of the constriction site, two things are kept in mind, the operational needs of the endoscopic procedure as already explained in this paragraph and the anticipated cavity wall contraction and expansion movements. Thus, in those endoscopic procedures where mechanical stability of the cavity walls is important, the numerical value of the constriction site diameter D should be relatively smaller.

Referring to FIGS. 3 to 7, the inflow tube 10 and the outflow tube 12 have been shown connected to the inlet and the outlet openings of a cavity 18 however such description is proposed only for the sake of an easier understanding of the system. In actual practice, the distal end of the inflow tube 10 is connected to an inflow port of a "continuous flow endoscope" and the proximal end of the outflow tube is connected to outflow port of the "continuous flow endoscope."

In the subsequent paragraphs the advantages and method of attaching and using the endoscope 27 with the described fluid management system shall be discussed.

The Advantages and the Method of Attaching the Endoscope with the Fluid Management System FIG. 1 shows the main block diagram of the invention. FIG. 1 is similar to FIG. 3 except that the tissue cavity 18 has been substituted by the endoscope 27. Though tissue cavity 18 has not been included in this figure, it is deemed to be understood that the distal end of the endoscope 27 is has been inserted via a single natural or a single created opening in the cavity. The distal open end of the inflow tube 10 has been shown connected to the inflow port 33 of the endoscope 27. The proximal open end of the outflow tube 12 has been connected to the outflow port 42 of the endoscope 27.

The fluid management system as described in FIGS. 3, 4, 6 and 7 removes fluid from the tissue cavity 18 by a process of active extraction and not by passive expulsion and such arrangement prevents the cavity 18 from collapsing despite the relatively large lumen diameter of the outflow port 42.

The arrangement shown in FIG. 1 provides a system of distending a body tissue cavity by continuous flow irrigation such that the detached tissue pieces and waste fluid present inside the cavity 18 is continuously evacuated via a single same outflow port 42 without the need of withdrawing the endoscope or a part of the endoscope, such as the endoscopic instrument, from the tissue cavity. The evacuated tissue pieces and the waste fluid is finally transported to the waste fluid collecting container 16 via the outflow tube 12 and the waste fluid carrying tube 45. Such an arrangement as shown in FIG. 1 also provides other benefits such as maintaining constant clear endoscopic visualization of the interior of the cavity, maintaining a constant cavity pressure and maintaining a constant mechanical distention of the cavity. The most important, especially in context with the invented system, is that the tissue cavity does not collapse despite a relatively large lumen diameter of the instrument 32 and the outflow port 42. Besides these benefits, the arrangement of FIG. 1 provides multiple other benefits such as determining the real time rate of fluid intravasation. In FIG. 1, in case the outflow pump 14 is removed and the distal end of the outflow tube 12 is made to open directly in atmosphere the cavity would tend to collapse intermittently during an endoscopic procedure, and such an arrangement as seen in the prior art systems has been described in the previous paragraph as "passive expulsion."

Referring to FIG. 1, a remote possibility could be proposed wherein the detached tissue pieces block the lumen 41 or the outflow port 42 of the instrument 32. In case of the remote possibility the outflow pump 14, or preferably both pumps 14, 5 could be made to rotate simultaneously in an opposite direction, that is in a direction opposite to the direction of the curved arrows, at a relatively high flow rate and for a relatively short period of time and such action is being termed as "flushing maneuver." The "flushing maneuver" would immediately flush the blocking tissue back into the tissue cavity and normal surgery could continue after this. The "flushing maneuver" could be initiated manually by the surgeon for example by a foot switch. The "flushing maneuver" could also be initiated by the help of a "pressure feedback mechanism" which would require an appropriate programming of the controller. The "pressure feedback mechanism" could utilize the optional outflow pressure transducer 26, or both the pressure transducers 26 and 17.

The endoscope 27 has been included in FIG. 1 but it is also deemed to be included in FIGS. 3, 4, 6 and 7 as well.

Referring to FIG. 1, both pumps, 5 and 14, and the endoscope 27 work in a synergistic manner such that both enhance the efficiency of either.

The invention is useful since it enhances the patient safety and surgical efficiency in continuous flow irrigation based endoscopic procedures.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of continuous flow irrigation of a tissue cavity during a morcellation based surgical procedure, comprising the steps of:
    providing a continuous flow irrigation endoscope in a vicinity of the tissue cavity, the endoscope comprising only a single housing sheath without an inner sheath, the single housing sheath having a longitudinal axis, a distal end and a proximal end; an inflow port located at the proximal end of the single housing sheath, configured to allow fluid to enter the single housing sheath; and a morcellator tube or a shaver tube or a cutter tube extending about parallel to the longitudinal axis of the single housing sheath, the morcellator tube or the shaver tube or the cutter tube being configured to move in at least one of a linear motion and a rotary motion relative to the longitudinal axis of the single housing sheath, wherein the morcellator tube or the shaver tube or the cutter tube includes an evacuation channel for removal of fluid and/or tissue debris traveling from a distal opening located at a distal end of the morcellator tube or the shaver tube or the cutter tube to an outflow port located at a proximal end of the tube, wherein the single housing sheath has an effective cross sectional area that comprises a total cross sectional area of the single housing sheath from which a cross sectional area occupied by the morcellator tube or the shaver tube or the cutter tube has been subtracted, and the morcellator tube or the shaver tube or the cutter tube has an effective cross sectional area denoted by a cross-sectional area of the evacuation channel, the effective cross sectional area of the single housing sheath being less than the effective cross sectional area of the morcellator tube or the shaver tube or the cutter tube;
    connecting the inflow port of the single housing sheath to a fluid source via an inflow pump for pumping fluid from the fluid source at a controlled inflow rate into the inflow port of the single housing sheath and the tissue cavity, wherein the inflow rate is a flow rate of the inflow pump; and
    connecting the outflow port of the tube directly and without any intermediate valve type system to an outflow pump for removing waste fluid from the tissue cavity at a controlled outflow rate, wherein the outflow rate is a flow rate of the outflow pump.

2. The method of claim 1, further comprising the step of providing a second tube having a controllable constriction site between the inflow port of the single housing sheath and a fluid source reservoir such that the second tube provides a route for any excess fluid being pumped by the inflow pump or due to physiologic contraction of walls of the tissue cavity, therefore avoiding turbulence inside the tissue cavity and maintaining a stable pressure inside the tissue cavity.

3. The method of claim 1, wherein the morcellation based surgical procedure is selected from a group consisting of hysteroscopic fibroid morcellation, trans uretheral prostate morcellation, hysteroscopic polyp morcellation, hysteroscopic septoplasty, hysteroscopic adhesiolysis, trans uretheral morcellation of bladder tumors, and arthroscopy.

4. The method of claim 1, wherein the inflow rate and the outflow rate are simultaneously increased or decreased without altering a pressure inside the tissue cavity.

5. A method of controlling pressure variations within a tissue cavity during a morcellation based surgical procedure, comprising the steps of:
    providing a continuous flow irrigation endoscope at least partially within the tissue cavity, the endoscope comprising only a single housing sheath without an inner sheath, the single housing having a longitudinal axis, a distal end and a proximal end; an inflow port located at the proximal end of the single housing sheath, configured to allow fluid to enter the single housing sheath; a morcellator tube or a shaver tube or a cutter tube extending about parallel to the longitudinal axis of the single housing sheath, wherein the morcellator tube or the shaver tube or the cutter tube includes an evacuation channel for removal of fluid and/or tissue debris traveling from a distal opening located at a distal end of the morcellator tube or the shaver tube or the cutter tube to an outflow port located at a proximal end of the tube, wherein the single housing sheath has an effective cross sectional area that comprises a total cross sectional area of the single housing sheath from which a cross sectional area occupied by the morcellator tube or the shaver tube or the cutter tube has been subtracted, and the morcellator tube or the shaver tube or the cutter tube has an effective cross sectional area denoted by a cross-sectional area of the evacuation channel, the effective cross sectional area of the single housing sheath being less than the effective cross sectional area of the morcellator tube or the shaver tube or the cutter tube;
    providing an inflow peristaltic pump in communication with the inflow port of the single housing sheath, to provide fluid into the tissue cavity;
    providing an outflow peristaltic pump in communication with the outflow port of the tube directly and without any intermediate valve type system, to remove fluid from the tissue cavity through the tube;
    selecting an outflow rotational speed for the outflow peristaltic pump;
    selecting a maximum flow rate at which fluid enters the tissue cavity and, based on the maximum flow rate, selecting an inflow rotational speed for the inflow peristaltic pump;
    activating the inflow peristaltic pump and the outflow peristaltic pump, to allow fluid to flow through the inflow port of the single housing sheath and into the tissue cavity, and from the tissue cavity through the outflow port of the tube, so that pressure inside the tissue cavity rises to a set pressure cavity; and
    maintaining the set pressure cavity for a period of time.

6. The method of claim 5, wherein the step of maintaining the set pressure cavity for a period of time is achieved by simultaneously increasing the inflow rotational speed and the outflow rotational speed by same numerical amount.

7. The method of claim 5, wherein the step of maintaining the set pressure cavity for a period of time is achieved by simultaneously decreasing the inflow rotational speed and the outflow rotational speed by same numerical amount.

8. The method of claim 5, wherein the set pressure cavity is independently maintained from the inflow rotational speed and the outflow rotational speed.

9. The method of claim 5, further comprising the step of providing a constriction tube having a controllable constriction site between the inflow port of the single housing sheath and the inflow pump such that the constriction tube provides a route for any excess fluid being pumped by the inflow pump or due to physiologic contraction of walls of the tissue cavity, therefore avoiding turbulence inside the tissue cavity and maintaining a stable pressure inside the tissue cavity.

10. The method of claim 9, further comprising the step of gradually reducing a diameter of the controllable constriction site to a fixed diameter until the set pressure cavity is achieved.

* * * * *